United States Patent [19]

Puttner et al.

[11] 4,320,125
[45] Mar. 16, 1982

[54] THIAZOLYLIDENE-OXO-PROPIONITRILE SALTS AND INSECTICIDAL COMPOSITIONS CONTAINING THESE SALTS

[75] Inventors: Reinhold Puttner; Ulrich Bühmann; Hartmut Joppien, all of Berlin, Fed. Rep. of Germany

[73] Assignee: Schering Aktiengesellschaft, Berlin and Bergkamen, Fed. Rep. of Germany

[21] Appl. No.: 149,449

[22] Filed: May 13, 1980

[30] Foreign Application Priority Data

May 17, 1979 [DE] Fed. Rep. of Germany ....... 2920182

[51] Int. Cl.³ .................... A01N 43/84; A01N 43/28; C07D 417/02; C07D 277/30
[52] U.S. Cl. ............................. 424/248.51; 424/263; 424/267; 424/270; 544/109; 546/194; 546/209; 546/256; 546/280; 548/205
[58] Field of Search ............... 544/109; 546/194, 209, 546/256, 280; 548/205; 424/248.51, 263, 267, 270

[56] References Cited

U.S. PATENT DOCUMENTS 4,153,705  5/1979  Puttner et al. .................... 548/205

FOREIGN PATENT DOCUMENTS 2703542  7/1978  Fed. Rep. of Germany .

Primary Examiner—John M. Ford
Assistant Examiner—R. W. Ramsuer
Attorney, Agent, or Firm—Michael J. Striker

[57] ABSTRACT

Thiazolylidene-oxo-propionitrile salt of the formula

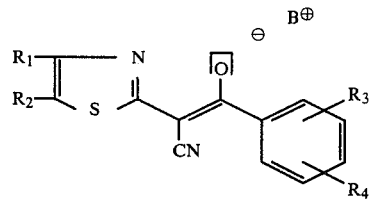

in which $R_1$, $R_2$ and $R_3$ have the meaning defined in the specification and $B^1$ is an ammonium group or an alkali cation. The compounds are valuable as insecticides of a superior activity against specific groups of insects.

17 Claims, No Drawings

THIAZOLYLIDENE-OXO-PROPIONITRILE SALTS AND INSECTICIDAL COMPOSITIONS CONTAINING THESE SALTS

BACKGROUND OF THE INVENTION

The invention relates to thiazolylidene-oxopropionitrile salts, insecticidal compositions containing these salts and process for making same.

Thiazolyl cinnamic acid nitriles with insecticidal activity have been disclosed in German published application No. 2,703,542. The action of these compounds, however, is not always adequate.

Likewise, compositions of a different chemical structure, but having similar activity are, for instance, phosphoric acid esters (West German Pat. No. 814,152), chlorinated hydrocarbons (West German Pat. No. 1,015,797), carbamates (U.S. Pat. No. 2,903,478) and pyrethroids (Belgian Pat. No. 857,859). These agents have usually a broad range of activity.

The object of the present invention is rather the development of an insecticide which has a narrow spectrum of activity and can be used successfully for controlling specific insects.

ESSENCE OF THE INVENTION

This object is met by an insecticidal agent which contains one or more compounds of the formula

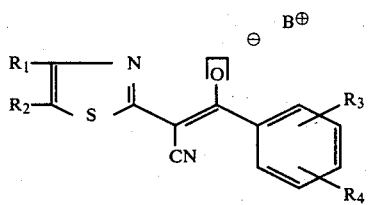

In this formula $R_1$ is hydrogen, halogen, $C_1$–$C_6$-alkyl, $C_3$–$C_6$-cycloalkyl, thienyl, pyridyl or phenyl substituted in one or several positions by the same or different radicals from the group constituted by $C_1$–$C_4$-alkyl, $C_1$–$C_4$-alkoxy, halogeno, trifluoromethyl, nitro and cyano.

$R_2$ is hydrogen, halogen, $C_1$–$C_6$-alkyl, $C_3$–$C_6$-cycloalkyl, thienyl, pyridyl, phenyl, or phenyl substituted in one or several positions by the same or different radicals selected from the group consisting of $C_1$–$C_4$-alkyl, $C_1$–$C_4$-alkoxy, halogeno, trifluoromethyl, nitro and cyano.

$R_3$ is hydrogen, $C_1$–$C_4$-alkyl, halogeno-$C_1$–$C_4$-alkyl, $C_1$–$C_4$-alkoxy, $C_1$–$C_4$-alkylthio, halogen, trifluoromethyl, nitro and cyano.

$R_4$ is hydrogen, halogen, trifluoromethyl, $C_1$–$C_4$-alkyl, $C_1$–$C_4$-halogenoalkyl, $C_1$–$C_4$-alkoxy, $C_1$–$C_4$-alkylthio, nitro, or cyano, and $B^\oplus$ is an ammonium group or an alkali cation.

The salts of the invention have a surprising insecticidal activity which partly is superior to the agents of analogous chemical constitution and they are highly effective against very specific insects.

A superior activity is found in the salts of the invention, particularly against pests of the genera Coleopterans, Lepidopterans, Dipterans and Rhynchotens which are economically of great significance.

The salts of the invention display their superior activity at concentrations of about 0.005 to 5.0%, preferably between 0.01 and 0.5%.

The salts of the invention can either be used by themselves or intermixed with each other or with other insecticidal agents. If desired, other plant protection agents or pesticides such as acaricides or fungicides may be added depending on the specific objective.

An increase of the intensity of activity and speed of activity can, for instance, be accomplished by additives such as organic solvents, wetting agents, and oils. Such additives therefore may permit a lowering of the dosage of the primary effective agent.

The compounds of their mixtures are preferably used in the form of compositions such as powders, spraying agents, granulates, solutions, emulsions or suspensions. Liquid and/or solid carrier materials or diluents may be added and, if desired, wetting agents, adhesion promoting agents, emulsifier and/or dispersants, may also be added.

Suitable liquid carriers are, for instance, water, aliphatic and aromatic hydrocarbons and furthermore cyclohexanone, isophorone, dimethylsulfoxide, dimethylformamide, and mineral oil fractions.

As solid carrier materials there may be used mineral earths, for instance tonsil, silicagel, talc, kaolin, attaclay, limestone, silicic acid and plant products such as flours.

There may also be added surface active agents such as calciumlignosulfonate, polyoxyethylene-alkylphenylethers, naphthalene sulfonic acids and their salts, phenolsulfonic acids and their salts, formaldehyde condensation products, fettyl alcoholsulfates, as well as substituted benzosulfonic acids and their salts.

The proportion of the active agent or agents in the different compositions can be varied within a broad range. The compositions may for instance contain about 5 to 95% by weight of active agent, about 95 to 5% by weight of liquid or carrier materials and, if desired, up to 20% by weight of surface active agents may be added upon a corresponding reduction of the carrier materials.

The application of the agents can be effected in conventional form, for instance with water as the carrier material in spray amounts of between 100 to 3000 l/ha (1 hectare = about 2.54 acres).

The application can be effected in the so-called low volume and ultra low volume procedure and also in the form of so-called microgranulates.

The making of these compositions can be effected in conventional form, for instance, by mixing or grinding processes. If desired, individual components can also be mixed only shortly prior to their use as this is for instance done in actual practice in the so-called tank mixing procedure.

Among the compounds of the invention, those are particularly outstanding with regard to their insecticidal action in which in the above equation $R_1$ is phenyl methylphenyl, halogenophenyl, trifluoromethylphenyl, methoxyphenyl, tert.-butyl or thienyl, $R_2$ is hydrogen, and $R_3$ and $R_4$ are hydrogen, halogen, methyl, trifluoromethyl, nitro or methoxy.

The salts may be cations of the formula

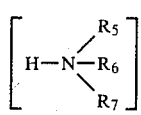

wherein $R_5$, $R_6$ and $R_7$ are the same or different and may be hydrogen or $C_1$-$C_6$-alkyl, $C_3$-$C_6$-alkenyl, $C_3$-$C_8$-cycloalkyl, benzyl, halogenobenzyl or $C_1$-$C_3$-alkylbenzyl, all of which radicals may have a hetero atom in one or several places of their chain. Two of the groups identified above as $R_5$, $R_6$ and $R_7$ may also form, together with the nitrogen atom, a heterocyclic 5-, 6-, 7- or 8-member ring which possibly may contain further heteroatoms such as oxygen, nitrogen, or sulfur. Particularly suited as cations of the salts of the invention are proton-type amines of the formula

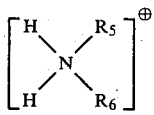

wherein $R_5$ and $R_6$ have the same meaning as above.

The alkali metal atoms may for instance be sodium or potassium.

These alkali salts are valuable intermediates for making other compounds which likewise are useful as insecticides. For this purpose the alkali salts are reacted with acylating agents of the formula

$R_8$—CO—X in which $R_8$ has the meaning which will presently be indicated and in which X is halogen, preferably chlorine.

More specifically, the acylated compounds of the formula

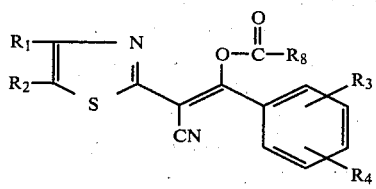

which can be produced from the sodium and potassium salts of the compounds of the invention are, for instance, compounds of the above formula wherein $R_1$, $R_2$, $R_3$ and $R_4$ have the meaning as above and $R_8$ is $C_1$-$C_6$-alkyl, $C_3$-$C_6$-cycloalkyl, $C_1$-$C_6$-alkoxy, $C_1$-$C_6$-alkylamino, $C_1$-$C_6$-dialkylamino, phenyl or is phenyl which is substituted in one or several places by the same or different radicals selected from the group consisting of $C_1$-$C_4$-alkyl, $C_1$-$C_4$-alkoxy, halogeno, trifluoromethyl, nitro and cyano.

PROCESS OF MAKING

The salts of the invention may, for instance, be made by reacting compounds of the formula

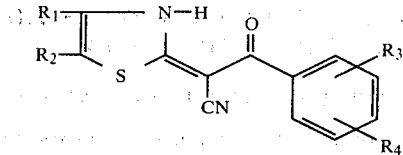

(a) If $B^\oplus$ is a quarternary ammonium group, with an amine of the formula

or (b) If $B^\oplus$ is an alkali cation with a base of the formula

B'Y.

In all these formulas $R_1$ to $R_7$ have the same meaning as above, B' is an alkali metal atom and Y is hydrogen or an organic residue.

In the case where $B^\oplus$ is an ammonium group the reaction is effected at temperatures between $-20°$ and $+100°$ C., preferably between $0°$ and $20°$ C. in about equimolar ratios and, if desired, in the presence of a solvent. As solvents there may be used alcohols, like methanol, ethanol and isopropanol; ethers, like diethylether and tetrahydrofuran; acid nitriles, like acetonitrile and acid amides, like dimethylformamide.

For the production of the alkali salts, sodium hydride is particularly suited as the base. The reaction in that case is effected preferably in an inert solvent such as tetrahydrofuran or dimethylformamide at temperatures between $-20°$ and $+80°$ C., preferably between $-10°$ and $+30°$ C.

The isolation of the formed salts of the invention is effected either by filtration or distilling off of the solvent employed or by precipitation with less polar organic solvents.

The following examples will further illustrate the making of the salts of the present invention.

EXAMPLE 1 n-butylammonium-[1-(2-chlorophenyl)-2-cyano-2-(4-phenylthiazole-2-yl)-ethenolate]

10.17 g (0.03 mol) of 3-(2-chlorophenyl)-3-oxo-2-(4-phenyl-2,3-dihydrothiazole-2-ylidene)-propionitrile were suspended in 15 ml dioxane and were reacted at 25° C. with 2.19 g (0.03 mol) n-butylamine. After short stirring a solution was formed. The solution was then concentrated in a vacuum and the residue was treated with a small amount of a cyclohexane-chloroform mixture. The crystals were removed by suction and digested with hot diisopropylether.

The yield was 7.5 g=60.7% of the theoretical amount.

m.p.: 194°–195° C.

In an analogous manner the following salts were formed:

| Compound | Physical constants |
|---|---|
| Dibutylammonium-[1-(2-chlorophenyl)-2-cyano-2-(4-phenyl- | m.p.: 163–165° C. |

-continued

| Compound | Physical constants |
|---|---|
| thiazole-2-yl)-ethanolate] | |
| Benzylammonium-[1-(2-chloro-phenyl)-2-cyano-2-(4-phenyl-thiazole-2-yl)-ethenolate] | m.p.: 161–163° C. |
| Piperidinium-[1-(2-chloro-phenyl)-2-cyano-2-(4-phenyl-thiazole-2-yl)-ethenolate] | m.p.: 155–157° C. |
| Pyrrolidinium-[1-(2-chloro-phenyl)-2-cyano-2-(4-phenyl-thiazole-2-yl)-ethenolate] | m.p.: 63–65° C. |
| Morpholinium-[1-(2-chloro-phenyl)-2-cyano-2-(4-phenyl-thiazole-2-yl)-ethenolate] | m.p.: 189–191° C. |
| Dimethylammonium-[1-(2-chloro-phenyl)-2-cyano-2-(4-phenyl-thiazole-2-yl)-ethenolate] | m.p.: 99–101° C. |
| Dihexylammonium-[1-(2-chloro-phenyl)-2-cyano-2-(4-phenyl-thiazole-2-yl)-ethenolate] | m.p.: 101–103° C. |
| Morpholinium-[2-cyano-1-(2-fluorophenyl)-2-(4-phenyl-thiazole-2-yl)-ethenolate] | m.p.: 172–173.5° C. |
| Dibutylammonium-1-(2-chloro-phenyl)-2-cyano-2-(4-phenyl-thiazole-2-yl)-ethenolate | m.p.: 175–176° C. |
| Dibutylammonium-[1-(2-chloro-phenyl)-2-cyano-2-(4-tert.-butylthiazole-2-yl)-ethenolate] | m.p.: 149–151° C. |
| Dibutylammonium-[2-cyano-2-(4-phenylthiazole-2-yl)-(2-trifluoromethylphenyl)-ethenolate] | m.p.: 134–137° C. |

The following example illustrates the making of the acylated thiazolyliden-oxo-propionitriles by use of the alkali salts of the present invention as the intermediate products.

EXAMPLE 2

3-benzoyloxy-2'-chloro-2-(4-phenyl-2-thiazolyl)-cinnamic acid nitrile 8.47 g (0.025 mol) of 3-(2-chlorophenyl)-3-oxo-2-(4-phenyl-2,3-dihydrothiazole-2-ylidene)-propionitrile dissolved in 30 ml tetrahydrofuran were added upon stirring at room temperature to a suspension of 0.66 g (0.0275 mol) of sodium hydride in 10 ml THF. The addition was effected dropwise. After 15 minutes stirring the mass was further reacted with 3.9 g (0.0275 mol) of benzoylchloride in 10 ml tetrahydrofuran. The solution was boiled for 10 minutes upon reflux and then filtered and finally concentrated in a vacuum up to dryness. After adding a small amount of chloroform, crystal forms which were removed by suction and digested three times with hot cyclohexane.

The yield was 7.1 g = 64.5% of the theoretical amount.

m.p.: 162°–164° C.

In an analogous manner the following compounds were made:

| Compound | Physical constants |
|---|---|
| 2'-chloro-3-(2-chlorobenzoyloxy)-2-(4-phenyl-2-thiazolyl)-cinnamic acid nitrile | m.p.: 122–124° C. |
| 2'-chloro-3-(methoxycarbonyloxy)-2-(4-phenyl-2-thiazolyl)-cinnamic acid nitrile | m.p.: 148–149° C. |
| 3-acetoxy-2-(4-phenyl-2-thiazolyl)-cinnamic acid nitrile | m.p.: 121–123° C. |
| (Z)-2'-chloro-3-dimethylamino-carbonyloxy-2-(4-phenyl-2- | m.p.: 113–115° C. |

-continued

| Compound | Physical constants |
|---|---|
| thiazolyl)-cinnamic acid nitrile | |
| 2'-chloro-3-(4-chlorobenzoyloxy)-2-(4-phenyl-2-thiazolyl)-cinnamic acid nitrile | m.p.: 175–177° C. |

The salts of the invention as well as the acylated products constituted normally non-smelling colorless crystalline bodies. They were practically insoluble in benzene and other unpolar organic solvents, but had a good solubility in dimethylformamide and dimethylsulfoxide.

The starting products for making the salts of the present invention are known and can be made by processes described in the prior art, for instance, by the process of the West German published application No. 2,703,542.

The following examples will further illustrate the application and activity of the compounds of the invention:

USE AND ACTIVITIES

EXAMPLE 3

The compounds of the inventions were used in this Example as aqueous suspensions in the concentration indicated in the Table below.

These active agents in the form of 4 mg of a spray/cm² were sprayed on cauliflower leaves disposed in polystyrene Petri dishes. After drying of the deposits 10 juvenile caterpillars of the cabbage moth (Plutella maculipennis) were placed into each Petri dish and the Petri dishes were closed for 2 days to leave the caterpillars with the feed indicated.

In the Table below the criteria for the activity was the mortality of the caterpillars stated in percentage after 2 days.

The following Table summarizes the results:

| Salts | Concentration of active agents in % | Mortality in % |
|---|---|---|
| Dibutylammonium-[1-(2-chloro-phenyl)-2-cyano-2-(4-phenyl-thiazole-2-yl)-ethenolate] | 0.1 | 100 |
| Benzylammonium-[1-(2-chloro-phenyl)-2-cyano-2-(4-phenyl-thiazole-2-yl)-ethenolate] | 0.1 | 100 |
| Piperidinium-[1-(2-chloro-phenyl)-2-cyano-2-(4-phenyl-thiazole-2-yl)-ethenolate] | 0.1 | 100 |
| Pyrrolidinium-[1-(2-chloro-phenyl)-2-cyano-2-(4-phenyl-thiazole-2-yl)-ethenolate] | 0.1 | 100 |
| n-butylammonium-[1-(2-chloro-phenyl)-2-cyano-2-(4-phenyl-thiazole-2-yl)]-ethenolate | 0.1 | 100 |
| Morpholinium-[1-(2-chloro-phenyl)-2-cyano-2-(4-phenyl-thiazole-2-yl)-ethenolate] | 0.1 | 100 |
| Dimethylammonium-[1-(2-chloro-phenyl)-2-cyano-2-(4-phenyl-thiazole-2-yl)-ethenolate] | 0.1 | 100 |
| Dihexylammonium-[1-(2-chloro-phenyl)-2-cyano-2-(4-phenyl-thiazole-2-yl)-ethenolate] | 0.1 | 100 |
| Morpholinium-[2-cyano-1-(2-fluorophenyl)-2-(4-phenyl-thiazole-2-yl)-ethenolate] | 0.1 | 100 |
| Dibutylammonium-1-(2-chloro-phenyl)-2-cyano-2-(4-phenyl-thiazole-2-yl)ethenolate | 0.1 | 100 |

-continued

| Salts | Concentration of active agents in % | Mortality in % |
|---|---|---|
| Dibutylammonium-[1-(2-chloro-phenyl)-2-cyano-2-(4-tert.-butylthiazole-2-yl)-ethenolate] | 0.1 | 100 |
| Dibutylammonium-[2-cyano-2-(4-phenylthiazole-2-yl)-(2-trifluoromethylphenyl)-ethenolate] | 0.1 | 100 |

EXAMPLE 4

The compounds of the invention were used in this example as aqueous suspensions in the concentration indicated in the Table below. The comparison compounds were likewise diluted with water so as to form suspensions or emulsions in the concentrations indicated.

These active agents were then sprayed in dosages of 4 mg spray amounts $cm^2$ into the lids and bottoms of polystyrene Petri dishes. To these spray deposits there were then exposed 25 adult Mediterranean fruit flies (Ceratitis capitata) per dish for 48 hours. The test was carried out in the laboratory with the Petri dishes closed and under conditions of a long-day illumination.

The criterium for the activity was the mortality of the flies expressed in percentages after 48 hours. The data appear from the following Table.

| Compound | Active agent concentration in % | Mortality in % |
|---|---|---|
| Dibutylammonium-[1-(2-chloro-phenyl)-2-cyano-2-(4-phenyl-thiazole-2-yl)-ethenolate] | 0.0025 | 88 |
| Piperidinium-[1-(2-chloro-phenyl)-2-cyano-2-(4-phenyl-thiazole-2-yl)-ethenolate] | 0.0025 | 88 |
| n-butylammonium-[1-(2-chloro-phenyl)-2-cyano-2-(4-phenyl-thiazole-2-yl)-ethenolate] | 0.0025 | 93 |
| Dimethylammonium-[1-(2-chloro-phenyl)-2-cyano-2-(4-phenyl-thiazole-2-yl)-ethenolate] | 0.0025 | 88 |
| Dihexylammonium-[1-(2-chloro-phenyl)-2-cyano-2-(4-phenyl-thiazole-2-yl)-ethenolate] | 0.0025 | 95 |
| Dibutylammonium-[2-cyano-2-(4-phenylthiazole-2-yl)-(2-trifluoromethylphenyl)-ethenolate] | 0.0025 | 100 |
| COMPARISON COMPOUNDS | | |
| 2'-chloro-3-hydroxy-2-(4-phenyl-2-thiazolyl)-cinnamic acid nitrile (West German published application 27 03 542) | 0.0025 | 73 |
| 2-(4-chlorophenyl)-isovaleric acid (α-cyano-3-phenoxybenzyl)-ester (Belgian Patent 857,859 | 0.0025 | 65 |
| 6,7,8,9,10-hexachloro-1,5,5a,6,9,9a-hexahydro-6,9-methano-2,4,3-benzodioxathiepine-3-oxide (West German Patent 1,015,797) | 0.0025 | 68 |

EXAMPLE 5

The compounds of the invention were used as aqueous suspensions in the concentrations indicated below. The comparison compounds were likewise diluted with water and used as suspensions or emulsions in the indicated concentrations.

These active agents were then sprayed in amounts of 4 mg of spray amounts/$cm^2$ on cauliflower leaves disposed in polystyrene Petri dishes. After drying of the spray deposits there were placed ten juvenile caterpillars of the cabbage moth (Plutella maculipennis) into each dish and the caterpillars were then left for 2 days in the closed Petri dishes with the indicated feed.

The criterium for the activity was the mortality of the caterpillar expressed in percentages after 2 days. The data are compiled in the following Table.

| | Concentration of active agent in % | Mortality in % |
|---|---|---|
| Salts | | |
| n-butylammonium-[1-(2-chloro-phenyl)-2-cyano-2-(4-phenyl-thiazole-2-yl)-ethenolate] | 0.01 | 100 |
| | 0.005 | 100 |
| Morpholinium-[1-(2-chloro-phenyl)-2-cyano-2-(4-phenyl-thiazole-2-yl)-ethenolate] | 0.01 | 100 |
| | 0.005 | 100 |
| Dibutylammonium-[2-cyano-2-(4-phenylthiazole-2-yl)-(2-trifluoromethylphenyl)-ethenolate] | 0.01 | 100 |
| | 0.005 | 100 |
| COMPARISON COMPOUNDS | | |
| 2'-bromo-3-hydroxy-2-(4-phenyl-2-thiazolyl)-cinnamic acid nitrile (West German published application 27 03 542) | 0.01 | 90 |
| | 0.005 | 50 |
| 1-naphthyl-methylcarbamate (U.S. Pat. No. 2,903,478) | 0.01 | 50 |
| | 0.005 | 10 |
| O,O-dimethyl-O-(p-nitro-phenyl)-thiono-phosphoric acid ester (West German Patent 814,152) | 0.01 | 70 |
| | 0.005 | 50 |

EXAMPLE 6

The salts of the present invention were used in the following example again as aqueous suspensions in the indicated concentrations. The comparison compound was diluted with water and also used as an emulsion.

These active agents were sprayed on wheat grains in doses of 4 mg of spray amount per $cm^2$. The wheat grains were placed in polystyrene Petri dishes in a form that they covered the bottom of the dish with a layer of a thickness of 1 grain. The sprays were then permitted to age in the air for 15 days. Thereupon they were exposed for 4 days to about 100 adult grain beatles (Sitophilus granarius) per Petri dish. The dishes were closed for this test.

The criterium for the evaluation was the mortality of the beatles expressed in percentages after a 4-day exposure. The results appear from the following table.

| | Concetration of active agent in % | Mortality in % after 4 days (15 day old spray deposit) |
|---|---|---|
| Salts | | |
| n-butylammonium-[1-(2-chlorophenyl)-2-cyano-2-(4-phenylthiazole-2-yl)-ethenolate] | 0.016 | 97 |
| | 0.0064 | 60 |
| Morpholinium-[1-(2-chloro-phenyl)-2-cyano-2-(4-phenyl-thiazole-2-yl)-ethenolate] | 0.016 | 92 |
| | 0.0064 | 65 |
| Dibutylammonium-[2-cyano-2-(4-phenylthiazole-2-yl)-(2-trifluoromethylphenyl)- | 0.016 | 100 |
| | 0.0064 | 75 |

| | Concetration of active agent in % | Mortality in % after 4 days (15 day old spray deposit) |
|---|---|---|
| ethenolate] | | |
| COMPARISON COMPOUNDS | | |
| O,O-dimethyl-O-(p-nitro-phenyl)-thionophosphoric acid ester (West German Paten 814,152) | 0.016 0.0064 | 100 13 |

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. Thiazolylidene-oxo-propionitrile salts of the formula

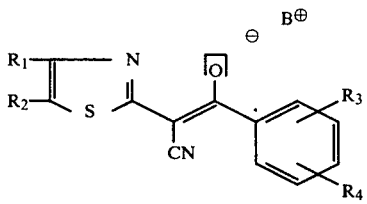

wherein
- $R_1$ is hydrogen, halogen, $C_1$–$C_6$-alkyl, $C_3$–$C_6$-cycloalkyl, thienyl, pyridyl or phenyl substituted in one or several positions by the same or different radicals from the group constituted by $C_1$–$C_4$-alkyl, $C_1$–$C_4$-alkoxy, halogeno, trifluoromethyl, nitro and cyano;
- $R_2$ is hydrogen, halogen, $C_1$–$C_6$-alkyl, $C_3$–$C_6$-cycloalkyl, thienyl, pyridyl, phenyl, or phenyl substituted in one or several positions by the same or different radicals selected from the group consisting of $C_1$–$C_4$-alkyl, $C_1$–$C_4$-alkoxy, halogeno, trifluoromethyl, nitro and cyano;
- $R_3$ is hydrogen, $C_1$–$C_4$-alkyl, halogeno-$C_1$–$C_4$-alkyl, $C_1$–$C_4$-alkoxy, $C_1$–$C_4$-alkylthio, halogen, trifluoromethyl, nitro and cyano;
- $R_4$ is hydrogen, halogen, trifluoromethyl, $C_1$–$C_4$-alkyl, $C_1$–$C_4$-halogenoalkyl, $C_1$–$C_4$-alkoxy, $C_1$–$C_4$-alkylthio, nitro or cyano, and
- $B^\oplus$ is an ammonium group or an alkali cation.

2. The thiazolylidene-oxo-propionitrile salts of claim 1 wherein
- $R_1$ is phenyl, methylphenyl, halogenophenyl, trifluoromethyl, methoxyphenyl, tert.-butyl or thienyl,
- $R_2$ is hydrogen,
- $R_3$ is hydrogen, halogen, methyl, trifluoromethyl, nitro or methoxy, and
- $R_4$ is the same as $R_3$.

3. The compounds of claim 1 wherein B is a cation of the formula

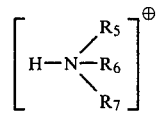

in which $R_5$, $R_6$ and $R_7$ are the same or different and stand for hydrogen or $C_1$–$C_6$-alkyl, $C_3$–$C_6$-alkenyl, $C_3$–$C_8$-cycloalkyl, benzyl, halogenbenzyl or $C_1$–$C_3$-alkylbenzyl which radicals may also have in their chain one or several heteroatoms, or wherein two of the groups $R_5$, $R_6$, and $R_7$ together with the nitrogen atom form a heterocyclic 5-, 6-, 7- or 8-member ring which may contain oxygen, nitrogen or sulfur as further heterogen atoms.

4. The salts or claim 1 wherein $B^\oplus$ is an alkali cation.

5. The compound of claim 1 which is n-butylammonium-[1-(2-chlorophenyl)-2-cyano-2-(4-phenylthiazole-2-yl)]-ethenolate.

6. The compound of claim 1 which is dibutylammonium-[1-(2-chlorophenyl)-2-cyano-2-(4-phenylthiazole-2-yl)-ethenolate].

7. The compound of claim 1 which is benzylammonium-[1-(2-chlorophenyl)-2-cyano-2-(4-phenylthiazole-2-yl)-ethenolate].

8. The compound of claim 1 which is piperidinium-[1-(2-chlorophenyl)-2-cyano-2-(4-phenylthiazole-2-yl)-ethenolate].

9. The compound of claim 1 which is pyrrolidinium-[1-(2-chlorophenyl)-2-cyano-2-(4-phenylthiazole-2-yl)-ethenolate].

10. The compound of claim 1 which is morpholinium-[1-(2-chlorophenyl)-2-cyano-2-(4-phenylthiazole-2-yl)-ethenolate].

11. The compound of claim 1 which is dimethylammonium-[1-(2-chlorophenyl)-2-cyano-2-(4-phenyl-thiazole-2-yl)-ethenolate].

12. The compound of claim 1 which is dihexylammonium-[1-(2-chlorophenyl)-2-cyano-2-(4-phenyl-thiazole-2-yl)-ethenolate].

13. The compound of claim 1 which is morpholinium-[2-cyano-1-(2-fluorophenyl)-2-(4-phenylthiazole-2-yl)-ethenolate].

14. The compound of claim 1 which is dibutylammonium-1-(2-chlorophenyl)-2-cyano-2-(4-phenyl-thiazole-2-yl)-ethenolate.

15. The compound of claim 1 which is dibutylammonium-[1-(2-chlorophenyl)-2-cyano-2-(4-tert.-butyl-thiazole-2-yl)-ethanolate].

16. The compound of claim 1 which is dibutylammonium-[2-cyano-2-(4-phenylthiazole-2-yl)(2-trifluoromethylphenyl)-ethenolate].

17. An insecticidal composition comprising about 5 to 95% by weight of an active agent as defined in claim 1 and about 95 to 5% by weight of liquid or solid carrier materials to which there may be added, upon corresponding reduction of the carrier materials, up to 20% by weight of surface active agents.

* * * * *